United States Patent [19]

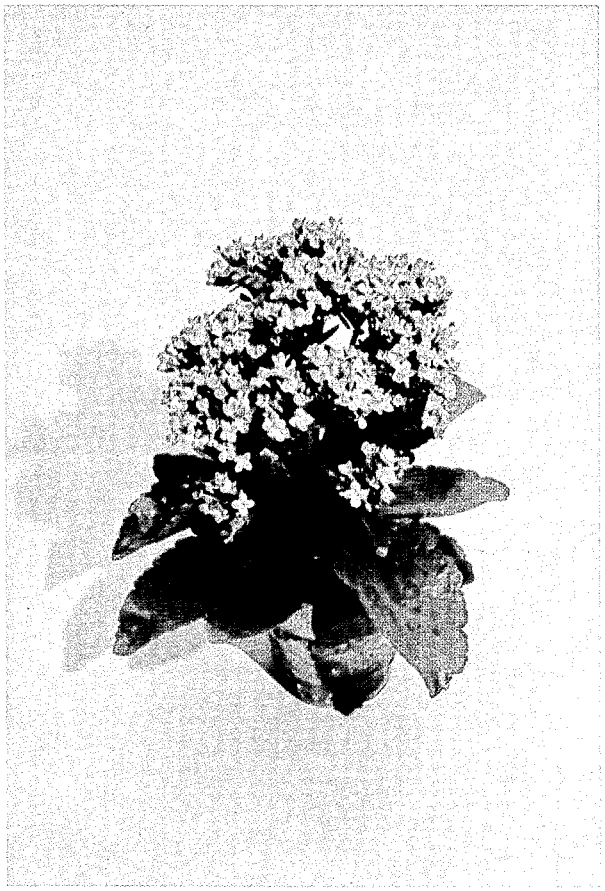

Grob

[11] Plant 4,101

[45] Sept. 13, 1977

[54] KALANCHOE PLANT

[75] Inventor: Adolf Grob, Saint Gall, Switzerland

[73] Assignee: Mikkelsens, Inc., Ashtabula, Ohio

[21] Appl. No.: 709,221

[22] Filed: July 27, 1976

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Donald D. Jeffery

[57] ABSTRACT

This invention relates to a novel Kalanchoe having fast but compact growth and relatively large, bright red flowers which are produced over a period of up to 2 months.

2 Drawing Figures

1

The present invention relates to a new and distinctive cultivar of Kalanchoe plant known by the cultivar name Jupiter. The new cultivar was developed by me in Saint Gall, Switzerland through controlled breeding by crossing the patented cultivar Feuerball (U.S. Plant Pat. No. 3,861), as the seed parent with an unnamed cultivar identified as clone No. 428 the pollen parent. Asexual reproduction by stem cuttings has shown that the unique features of this new Kalanchoe are stabilized and are reproduced true to type in successive propagations.

The following characteristics in combination distinguish the new Kalanchoe from both its parent varieties and other cultivated Kalanchoes of this type known and used in the floriculture industry:

1. In comparison to my patented cultivar Feuerball, my new cultivar is faster growing but maintains a similar compact growth.

2. In comparison to Feuerball, Jupiter has less branching but is above average for Kalanchoes. Jupiter tends to develop a large floral display with a minimum amount of basal growth required before removal of the apical tip. Jupiter branches quite well at flower initiation without removal of apical tip, a characteristic quite useful in producing small pot plants.

3. The leaves of Jupiter are larger than Feuerball but generally smaller than on my cultivars Feuerzauber, U.S. Plant Pat. No. 3,853, Rotkappchen, U.S. Plant Pat. No. 3,851, and Feuerwerk II, disclosed in my pending application filed herewith.

4. Jupiter is highly floriferous, approaching that of Feuerball, but has a slightly larger flower and deeper red color.

5. Flowering continues over a period of two months or more without giving an appearance of being past a salable condition.

6. Jupiter is very suitable for production as small flowering plants in 5 cm. to 8 cm. pots for combination planters, dish gardens, and terrariums.

7. Mother plants are very productive of vegetative cuttings that propagate very readily.

8. Size, type, and placement of foliage facilitate the wrapping of Jupiter's flowering plants for commercial distribution.

9. The very strong growth habit, large quantity of bright red flowers and easy growing requirements of Jupiter are of economic importance to commercial growers.

10. Early-medium flowering response, 11–12 weeks after short day treatment. Flowering continues over a period of 4–6 weeks.

2

11. Excellent disease resistance, especially in winter against stem-rot.

12. Full umbels, no faded single flowers visible since they are covered by new flowers.

The accompanying colored photograph illustrates the overall appearance of the new variety taken as a face view of the plant and showing the colors as true as it is reasonably possible to obtain in a colored reproduction of this type.

The following is a detailed description of my new Kalanchoe variety based on plants produced under commercial practices at the nursery of Wyss Samen und Pflanzen AG, CH-Zuchwil, Switzerland. Color references are made to the Royal Horticultural Society Colour Chart except where general terms of ordinary dictionary significance are used.

Parentage: Seedling of Feuerball and clone No. 428 (dark red).

Propagation:

*Type cutting.*—Vegetative tip cuttings 15 to 20 mm. long.

*Time to root.*—14–18 days at 20°–25° C summer.

*Time to root.*—20–24 days at 22° C winter.

*Rooting habit.*—Fast, abundant, fibrous, dendritic.

Plant Description:

*Form.*—Fully round, compact, and upright.

*Habit of growth.*—Fast growing, ample self-branching, excellent branching after pinching, flowers having excellent placement.

*Foliage description.*—Excellent quality foliage of moderate size, pleasing green color, opposite, slight cupping, nearly horizontal to stem. Size: 8 to 10 cm. long by 6 to 7 cm. wide leaf petiole 20 to 25 mm long. Some cupping may be either concave or convex. Shape: Young leaves oval to mature leaves ovate, apex obtuse, base obtuse. Texture: glabrous, coriaceous. Margin: doubly crenate. Color: mature foliage top side near 146-A underside between 148B and 147C.

Flowering description:

*Flowering habits.*—Central flowers of each section of compound paniculate cymes open first, followed progressively by surrounding flowers for period of 4 to 6 weeks.

*Natural flowering season.*—End of January at 18°. Flowering time under controlled daylength at 18°–20° C; in summer is 11–12 weeks; in winter is 12–13 weeks. Flowering is progressive from the central terminal flower outwardly for 5–8 weeks.

*Flower bud description.*—Cylindrical with basal bulge totaling 10–14 mm. in length before opening, showing light red reverse coloring.

*Flowers borne.*—On heavy strong peduncles, somewhat short, 10–12 cm., 8–10 mm. in diameter, that branch out with opposite pedicels varying in length from 1 to 3 cm; flowers do not shatter.

*Quantity of flowers.*—Main terminal compound cymes have 80 to 150 flowers.

*Petals.*—Shape: nearly round, 5 mm. Color: top side when opening, between red 44A and 43B, fading to red 42C; underside; near red 38A. Number of petals: four, total flower size 12–13 mm. in diameter.

*Reproductive organs.*—Stamens: number $2 \times 4 = 8$. Anther shape: flat, color, light brown; Filament color: cream/yellow green; Pollen color: yellow. Pistils: Stigma shape: irregular, color white crystalline; Style color: translucent green; Ovaries: number 4, size 6 mm, color green, total length pistel 10 mm.

Disease resistance: Very resistant to winter crown and stem rot and moderately resistant to powdery mildew.

It should be noted that environmental conditions such as temperature, light, and especially soil moisture and nutrients greatly affect the size and color of foliage and flowers of Kalanchoes because of their succulent type of growth.

I claim:

1. A new and distinct cultivar of Kalanchoe plant characterized particularly as to uniqueness by the combined characteristics of fast and compact growth; develops a large floral display with a minimum amount of basal growth required before removal of the apical tip; a relatively large flower having a bright red color; continuous flowering over a period of up to two months; suitable for production as small plants for pots, and by its production of vegetative cuttings that propagate very readily.

* * * * *

UNITED STATES PATENT AND TRADEMARK OFFICE

CERTIFICATE OF CORRECTION

PATENT NO. : PP-4101

DATED : September 13, 1977

INVENTOR(S) : ADOLF GROB

It is certified that error appears in the above-identified patent and that said Letters Patent are hereby corrected as shown below:

In Column 1, line 5, "Gall" should be --Gallen--.

Signed and Sealed this

*Twenty-eighth* Day of *February 1978*

[SEAL]

*Attest:*

RUTH C. MASON
*Attesting Officer*

LUTRELLE F. PARKER
*Acting Commissioner of Patents and Trademarks*